(12) United States Patent
Yamayoshi

(10) Patent No.: US 6,201,249 B1
(45) Date of Patent: Mar. 13, 2001

(54) X-RAY IMAGING SYSTEM

(75) Inventor: Junichi Yamayoshi, Urawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/170,654

(22) Filed: Oct. 14, 1998

(30) Foreign Application Priority Data

Oct. 16, 1997 (JP) .................................................. 9-283606

(51) Int. Cl.$^7$ .................................................. H05G 1/26
(52) U.S. Cl. .............................. 250/370.11; 250/370.09; 250/370.14
(58) Field of Search .......................... 250/370.11, 370.09, 250/370.14

(56) References Cited

U.S. PATENT DOCUMENTS

| | | | | |
|---|---|---|---|---|
| 5,661,309 | * | 8/1997 | Jeromin et al. ................. | 250/370.09 |
| 5,841,833 | * | 11/1998 | Mazess et al. .................. | 250/370.09 |
| 5,877,501 | * | 3/1999 | Ivan et al. ....................... | 250/370.09 |
| 5,881,162 | * | 3/1999 | Ishimitsu ......................... | 250/370.09 |
| 6,031,892 | * | 2/2000 | Karellas ........................... | 250/370.11 |
| 6,044,131 | * | 3/2000 | McEvoy et al. ................. | 378/162 |

* cited by examiner

Primary Examiner—Constantine Hannaher
Assistant Examiner—Otilia Gabor
(74) Attorney, Agent, or Firm—Fitzpatrick, Cella, Harper & Scinto

(57) ABSTRACT

An X-ray imaging system includes an X-ray sensor having an imaging section for picking up an X-ray image, and a controller for controlling the X-ray sensor and processing an image supplied by the X-ray sensor. The X-ray sensor has a non-volatile storage device for storing information by which the controller specifies conditions of imaging performed by the imaging section, and the controller has a decision unit for reading out the information stored on the non-volatile storage device and deciding, on the basis of the information, a method of controlling the X-ray sensor and/or content of processing executed by the controller.

33 Claims, 6 Drawing Sheets

X-RAY IMAGING SYSTEM

BACKGROUND OF THE INVENTION

1. Field of the Invention

This invention relates to an X-ray image sensing unit, a processing unit used upon being connected to the X-ray image sensing unit, and an X-ray imaging system obtained by combining the X-ray image sensing unit and the processing unit. The present invention is ideal for application to a digital X-ray imaging apparatus that uses a solid-state imaging device, particularly a digital X-ray imaging apparatus in which the sensor section for imaging is capable of being separated from a processing unit such as a controller.

2. Description of the Related Art

A film screen system comprising a combination of sensitized paper and X-ray photographic film is used in X-ray imaging for the purpose of medical diagnosis. In accordance with this system, X-rays that have passed through an object include information representing the interior of the object and are converted by the sensitized paper to visible light proportional to the strength of the X-rays. The visible light exposes the X-ray photographic film so that an X-ray image is formed on the film.

A digital X-ray imaging apparatus that has recently begun to be used employs a phosphor to convert X-rays to visible light that is proportional to the strength of the X-rays, converts the visible light to an electric signal using a photoelectric transducer, and converts the electric signal from an analog to a digital quantity by an A/D converter.

SUMMARY OF THE INVENTION

An object of the present invention is to make it possible for a processing unit to automatically acquire information relating to imaging by the imaging section of an X-ray image sensing unit in an X-ray imaging system having the X-ray image sensing unit and the processing unit.

According to a first aspect of the present invention, the foregoing object is attained by providing an X-ray image sensing unit having an imaging section for picking up an X-ray image, the X-ray imaging sensing unit being removably attached to an external processing unit and comprising: transfer means for transferring the image picked up by the imaging section to the processing unit; a terminal for connecting or disconnecting the transfer means and the processing unit; and a non-volatile storage medium for storing information by which the processing unit specifies conditions of imaging by the imaging section.

In a preferred embodiment, the information stored on the storage medium in the X-ray imaging sensing unit according to the first aspect of the invention includes e.g. information relating to sensitivity of the imaging section.

In a preferred embodiment, the information stored on the storage medium in the X-ray imaging sensing unit according to the first aspect of the invention includes e.g. information relating to sharpness of the image picked up by the imaging section.

In a preferred embodiment, the imaging section in the X-ray imaging sensing unit according to the first aspect of the invention has a phosphor for converting X-rays to visible light and a photoelectric transducer for converting the visible light to electricity, the information stored on the storage medium including e.g. information relating to thickness of the phosphor.

In a preferred embodiment, the information stored on the storage medium in the X-ray imaging sensing unit according to the first aspect of the invention includes e.g. information relating to defective pixels of the imaging section.

In a preferred embodiment, the information stored on the storage medium in the X-ray imaging sensing unit according to the first aspect of the invention includes e.g. information relating to ON time of the imaging section.

In a preferred embodiment, the information stored on the storage medium in the X-ray imaging sensing unit according to the first aspect of the invention includes e.g. information for compensating for a difference insensitivity between elements constituting pixels of the imaging section.

In a preferred embodiment, the information stored on the storage medium in the X-ray imaging sensing unit according to the first aspect of the invention includes e.g. information indicating whether the X-ray imaging sensing unit has means for controlling X-ray exposure time.

In a preferred embodiment, the information stored on the storage medium in the X-ray imaging sensing unit according to the first aspect of the invention includes e.g. information indicating whether the X-ray imaging sensing unit has a grid for preventing X-rays, which have been scattered by an object, from impinging upon the imaging section.

In a preferred embodiment, the X-ray imaging sensing unit according to the first aspect of the invention further comprises a grid for preventing X-rays, which have been scattered by an object, from impinging upon the imaging section, wherein the information stored on the storage medium includes e.g. information relating to the type of grid.

In a preferred embodiment, the information stored on the storage medium in the X-ray imaging sensing unit according to the first aspect of the invention includes e.g. an ID number of the X-ray imaging sensing unit.

In a preferred embodiment, the storage medium in the X-ray imaging sensing unit according to the first aspect of the invention is capable of having information read out and rewritten by the processing unit.

According to a second aspect of the present invention, the foregoing object is attained by providing an X-ray imaging system comprising an X-ray imaging sensing unit having an imaging section for picking up an X-ray image, and a processing unit for controlling the X-ray imaging sensing unit and processing an image supplied by the X-ray imaging sensing unit, wherein the X-ray imaging sensing unit has a non-volatile storage medium for storing information by which the processing unit specifies conditions of imaging by the imaging section, and the processing unit has decision means for reading out the information stored on the storage medium and deciding, on the basis of the information, a method of controlling the X-ray imaging sensing unit and/or content of processing executed by the processing unit.

In a preferred embodiment, the X-ray imaging sensing unit in the X-ray imaging system according to the second aspect of the invention is capable of being attached and detached, and the X-ray imaging sensing unit and processing unit each have a terminal for connecting and disconnecting them.

In a preferred embodiment, the processing unit in the X-ray imaging system according to the second aspect of the invention has a function whereby a storage device on a network is shared by other processing units.

In a preferred embodiment of the X-ray imaging system according to the second aspect of the invention, an ID number of the X-ray imaging sensing unit is stored on the storage medium, information indicating conditions of imaging by imaging sections of various X-ray imaging sensing units is stored in the storage device on the network, and the processing unit reads the ID number out of the storage medium and reads information corresponding to this ID number out of the storage device on the network.

In a preferred embodiment of the X-ray imaging system according to the second aspect of the invention, the processing unit has a mechanism for connecting the processing unit to a plurality of X-ray imaging sensing units.

In a preferred embodiment of the X-ray imaging system according to the second aspect of the invention, the information stored on the storage medium includes information relating to sensitivity of the imaging section.

In a preferred embodiment of the X-ray imaging system according to the second aspect of the invention, the information stored on the storage medium includes information relating to sharpness of the image picked up by the imaging section.

In a preferred embodiment of the X-ray imaging system according to the second aspect of the invention, the imaging section has a phosphor for converting X-rays to visible light and a photoelectric transducer for converting the visible light to electricity, the information stored on the storage medium including e.g. information relating to thickness of the phosphor.

In a preferred embodiment of the X-ray imaging system according to the second aspect of the invention, the information stored on the storage medium includes e.g. information relating to defective pixels of the imaging section.

In a preferred embodiment of the X-ray imaging system according to the second aspect of the invention, the information stored on the storage medium includes e.g. information relating to ON time of the imaging section.

In a preferred embodiment of the X-ray imaging system according to the second aspect of the invention, the information stored on the storage medium in the X-ray imaging sensing unit includes e.g. information for compensating for a difference in sensitivity between elements constituting pixels of the imaging section.

In a preferred embodiment of the X-ray imaging system according to the second aspect of the invention, the information stored on the storage medium in the X-ray imaging sensing unit includes e.g. information indicating whether the X-ray imaging sensing unit has means for controlling X-ray exposure time.

In a preferred embodiment of the X-ray imaging system according to the second aspect of the invention, the information stored on the storage medium includes e.g. information indicating whether the X-ray imaging sensing unit has a grid for preventing X-rays, which have been scattered by an object, from impinging upon the imaging section.

In a preferred embodiment of the X-ray imaging system according to the second aspect of the invention, the X-ray imaging sensing unit further includes a grid for preventing X-rays, which have been scattered by an object, from impinging upon the imaging section, wherein the information stored on the storage medium includes e.g. information relating to the type of grid.

In a preferred embodiment of the X-ray imaging system according to the second aspect of the invention, the storage medium is capable of having information read out and rewritten by the processing unit.

According to a third aspect of the present invention, the foregoing object is attained by providing a processing unit, which is connected to one or a plurality of X-ray imaging sensing units having an imaging section for picking up an X-ray image, for controlling the X-ray imaging sensing unit and processing an image supplied by the X-ray imaging sensing unit, the processing unit having decision means for reading out information, which is for specifying conditions of imaging by the imaging section, from a non-volatile storage medium possessed by the X-ray imaging sensing unit, and deciding, on the basis of this information, a method of controlling the X-ray imaging sensing unit and/or content of processing executed by the processing unit.

In a preferred embodiment of the processing unit according to the third aspect of the invention, the decision means decides, on the basis of the above-mentioned information, content of sensitivity adjustment processing applied to an image supplied by the X-ray imaging sensing unit.

In a preferred embodiment of the processing unit according to the third aspect of the invention, the decision means decides, on the basis of the above-mentioned information, content of image sharpening processing applied to an image supplied by the X-ray imaging sensing unit.

In a preferred embodiment of the processing unit according to the third aspect of the invention, the decision means decides, on the basis of the above-mentioned information, content of processing for interpolating defective pixels in an image supplied by the X-ray imaging sensing unit.

In a preferred embodiment of the processing unit according to the third aspect of the invention, the decision means decides, on the basis of the above-mentioned information, content of processing for correcting a difference in sensitivity between elements constituting pixels of the imaging section.

In a preferred embodiment of the processing unit according to the third aspect of the invention, the decision means decides, on the basis of the above-mentioned information, whether to issue a warning to the user.

In a preferred embodiment of the processing unit according to the third aspect of the invention, the decision means decides, on the basis of the above-mentioned information, a method of controlling X-ray exposure time.

In a preferred embodiment of the processing unit according to the third aspect of the invention, the decision means judges, based upon the above-mentioned information, whether the X-ray imaging sensing unit has a grid for preventing X-rays, which have been scattered by an object, from impinging upon the imaging section, and decides, based upon the judgment made, whether stripe-removal processing is to be applied to an image supplied by the X-ray imaging sensing unit.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Figure 1:
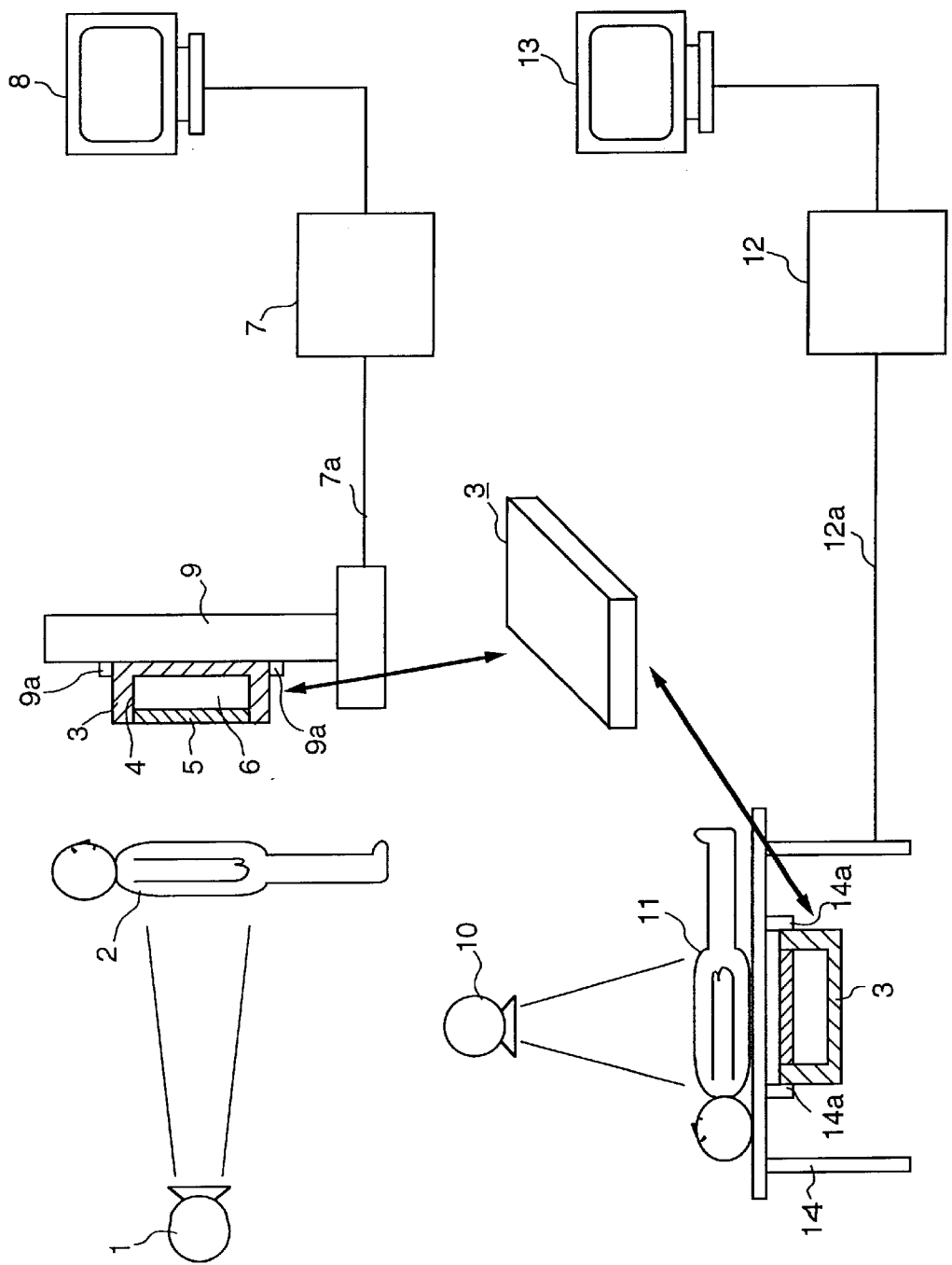
FIG. 1 is a diagram schematically illustrating the overall configuration of an X-ray imaging system according to a first embodiment of the present invention.

FIG. 1 is a diagram schematically illustrating the overall configuration of an X-ray imaging system according to a first embodiment of the present invention.

Shown in FIG. 1 are X-ray generating devices 1, 10, objects 2, 11 such as human patients, an X-ray sensor (X-ray imaging sensing unit) 3, a solid-state imaging device 4 provided inside the X-ray sensor 3, a phosphor 5 and a photoelectric transducer 6 constructing the solid-state imaging device 4, controllers (processing units) 7, 12 such as work stations, display units 8, 13 such as monitors, a stand 9 for upright imaging, and a stand 14 serving as a bed. The controllers 7 and 12 function as control units for controlling the X-ray sensor 3 and as image processors for processing an image supplied by the X-ray sensor 3.

Discussed first will be a case where the X-ray sensor 3 is attached to the stand 9 and an upright image of the object 2 is captured with the plane of X-ray incidence of the X-ray sensor 3 being in a substantially vertical attitude.

X-rays output by the X-ray generating device 1 pass through the object 2 and impinge upon the X-ray sensor 3 attached to the stand 9. The impinging X-rays contain information representing the interior of the object 2 and are converted to visible light, which is proportional to the strength of the X-rays, by the phosphor 5 of the solid-state imaging device 4 inside the X-ray sensor 3. The visible light is converted by the photoelectric transducer 6 to a voltage (electric charge) proportional to the strength of the visible light. The voltage is converted to a digital quantity by an A/D converter (not shown) within the X-ray sensor 3, and the digital image data thus obtained is transferred to the controller 7. An image is displayed on the display unit 8 in accordance with the image data transferred.

The X-ray sensor 3 can be detached from the stand 9 and attached to the stand 14. In this case the X-ray sensor 3 is connected to the controller 12. The X-ray sensor 3 is attached to the stand 14, the plane of X-ray incidence of the X-ray sensor 3 is faced upward and placed in a substantially horizontal attitude, and the object 11 is irradiated with X-rays emitted by the X-ray generating device 10 disposed above the stand 14, whereby an X-ray image of the prone object 11 can be captured in the same manner as the upright object.

Though the A/D conversion is performed within the X-ray sensor 3 in this embodiment, the conversion can be carried out by the controller 7, by way of example.

Figure 2:
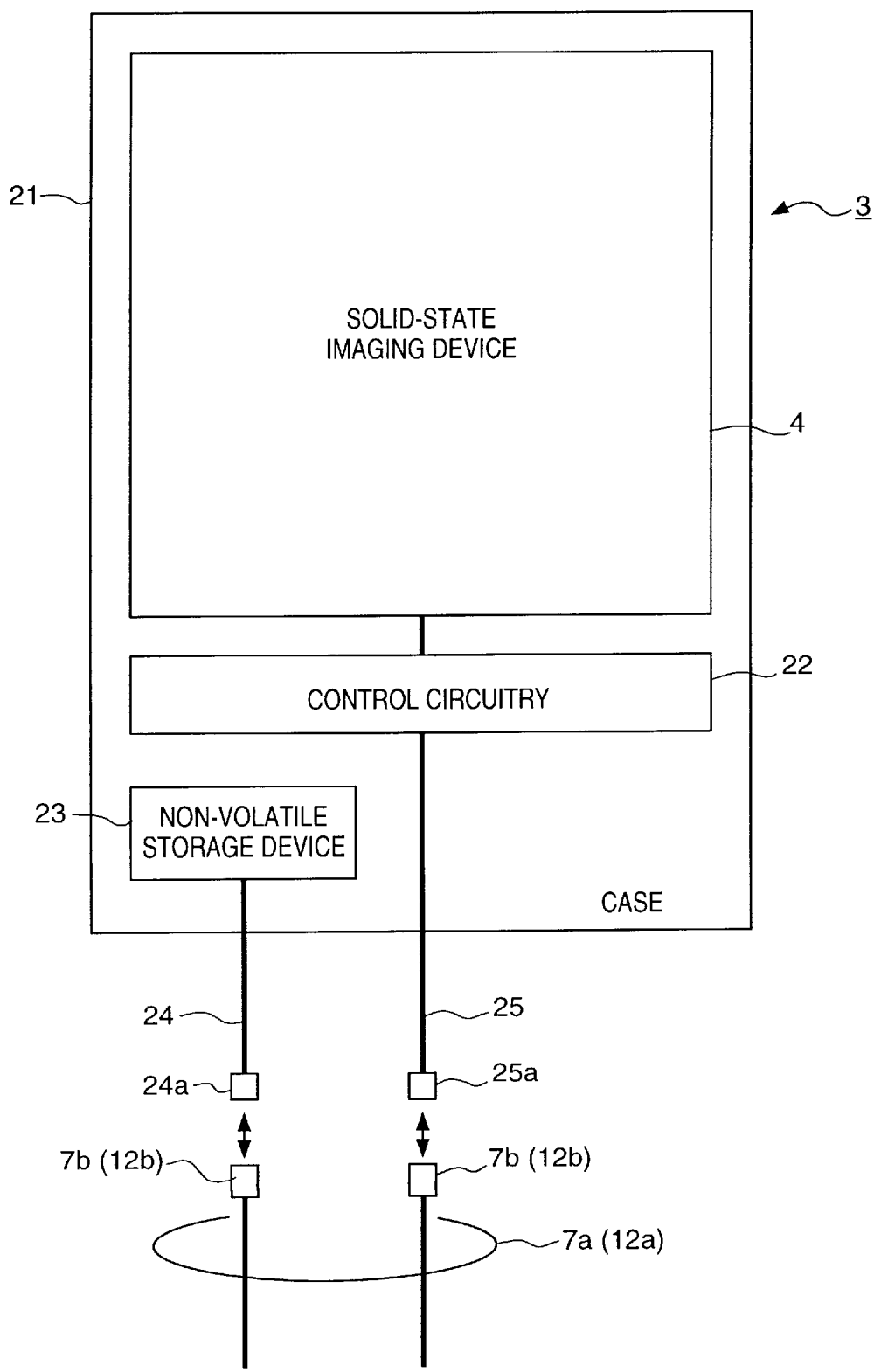
FIG. 2 is a diagram showing an X-ray sensor (X-ray imaging sensing unit)

FIG. 2 is a diagram schematically illustrating the internal structure of the X-ray sensor 3.

The X-ray sensor 3 has a case 21 made of a carbon-based material, for example, for the purpose of allowing transmission of X-rays without attenuation. The solid-state imaging device 4 is obtained by affixing a phosphor, which converts X-ray to visible light, on the surface of a photoelectric conversion device comprising a multiplicity of photoelectric transducers arrayed in the form of a matrix over the entirety of the rectangular area shown in FIG. 2.

The X-ray sensor 3 further includes a control electric circuit (transfer unit) 22 for controlling the solid-state imaging device 4, and a non-volatile storage device 23 for storing information specific to the X-ray sensor 3. The solid-state imaging device 4, control electric circuit 22 and non-volatile storage device 23 are disposed inside the case 21 of the X-ray sensor 3.

Ideal examples of the non-volatile storage device 23 are a magnetic disk that retains its content regardless of whether the power supply is on or off, an EEPROM or a semiconductor memory backed up by a battery. If intervals during which the power supply is off are comparatively short, it is also possible to use a semiconductor memory of the type in which electric charge is accumulated in a capacitor when the power supply is on and then use the accumulated charge as a power supply for retaining information when the power supply is off.

The solid-state imaging device 4 is connected to the controller 7 or 12 externally of the X-ray sensor 3 via the control electric circuit 22 and a signal cable 25. As a result, the controller 7 or 12 is capable of receiving image data from the solid-state imaging device 4 via the control electric circuit 22 and cable 25. The non-volatile storage device 23 is connected to the controller 7 or 12 via a signal cable 24 including a control signal line for access, a power supply line and a data line. As a result, the controller 7 or 12 is capable of reading data out of the non-volatile storage device 23 and of writing data to the non-volatile storage device 23.

Various mechanisms can be adopted to connect and disconnect the signal cables 24 and 25 to and from the controller 7 (or 12). For example, it is possible to adopt an arrangement in which electrical contacts (terminals) 7b (or 12b) connected to a signal cable 7a (or 12a) of the controller 7 (or 12) are provided on the stand 9 (or 14) at a prescribed position. The X-ray sensor 3 is mounted on a mounting portion 9a (or 14a) of the stand 9 (or 14), whereby electrical contacts (terminals) 24a and 25a at the ends of the signal cables 24 and 25 are brought into contact with electrical contacts 7b (or 12b). Further, by way of example, it is possible to adopt an arrangement in which connectors (terminals) 24a and 25a at the ends of the signal cables 24 and 25 and connectors (terminals) 7b (or 12b) at the end of the signal cable 7a (or 12a) are connected by the user.

Figure 6:
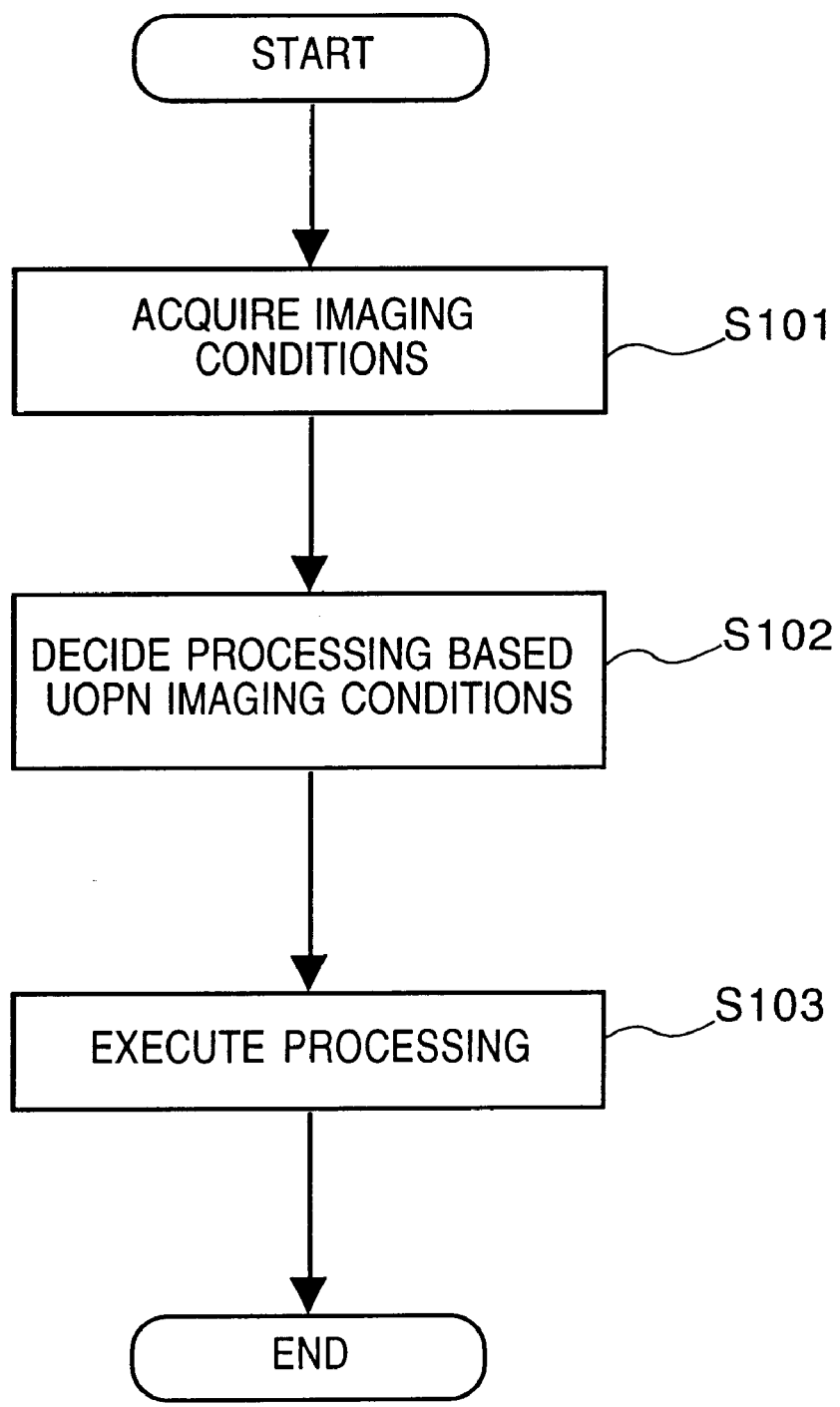
FIG. 6 is a flowchart illustrating processing executed by a controller in the first through fourth embodiments of the present invention.

Processing executed by the controller 7 or 12 will be described next. FIG. 6 is a flowchart illustrating the flow in the controller 7 or 12. The processing shown in this flowchart is executed based upon software that has been stored in a memory within the controller 7 or 12.

First, the controller 7 or 12 accesses the non-volatile storage device 23 of the X-ray sensor 3, whereby information relating to the imaging conditions of the solid-state imaging device 4 are acquired (S101). Next, on the basis of the information relating to the imaging conditions, the controller 7 or 12 decides the content of processing such as the method of controlling the X-ray sensor 3 and the content of image processing (S102). This is followed by S103, at which the controller 7 or 12 executes processing corresponding to the decision rendered.

One example of the information acquired by accessing the non-volatile storage device 23 is the type of phosphor 5. Though the phosphor 5 is used to convert X-ray to visible light, as mentioned above, the conversion efficiency thereof differs depending upon the type and thickness of the material. Increasing the thickness of the phosphor 5 raises its sensitivity to X-rays but a decline in sharpness occurs due to image blurring. Conversely, reducing the thickness of the phosphor 5 lowers its sensitivity to X-rays but increases sharpness. In order for the phosphor to be used selectively in line with user preference and in order for the X-ray images obtained to manifest their different characteristics, it is required that the image processing executed by the controller 7 or 12 conform to the particular type of phosphor.

Consider first a case where the information concerning the type of phosphor 5 that the controller 7 or 12 has obtained from the non-volatile storage device 23 indicates that the phosphor 5 is thick, i.e., that the material will present an image of little sharpness. In this case the image captured will exhibit a low overall sharpness. The controller 7 or 12, therefore, subjects the image data obtained via the signal cable 25 to processing for producing better sharpness (S102, S103).

Next, consider a case where the information concerning the type of phosphor 5 that the controller 7 or 12 has obtained from the non-volatile storage device 23 indicates that the phosphor 5 is thin, i.e., that the material will present a sharp image. In this case the image captured will exhibit a low overall sensitivity. The controller 7 or 12, therefore, subjects the image data obtained via the signal cable 25 to processing that reduces the sharpness of the image and raises overall sensitivity instead (S102, S103).

Information directly indicating sensitivity or sharpness may be stored in the non-volatile storage device 23. Alternatively, phosphor thickness may be normalized to a prescribed number of stages. Then, when the device is manufactured, stage information indicating the particular normalized stage to which the thickness of the phosphor belongs may be stored in the non-volatile storage device 23. In the latter case, the controller 7 or 12 is capable of acquiring sensitivity or sharpness by performing a calculation or referring to a table on the basis of stage information. Processing applied to image data to improve sharpness or raise sensitivity is well known and need not be described here.

There are occasions where it is necessary to update the information in the non-volatile storage device 23, as when the sensitivity of the phosphor 5 experiences a marked decline with the passage of time. In such case the controller 7 or 12 rewrites the information. For example, the controller 7 or 12 diagnoses the sensitivity of the phosphor periodically and, if there is a change in the sensitivity data obtained, rewrites the sensitivity information in the non-volatile storage device 23 on the basis of the sensitivity data. It will suffice to execute processing of the image data based upon the rewritten sensitivity information.

The image represented by the image data processed by the controller 7 or 12 is displayed on the display unit 8 or 13.

The non-volatile storage device 23 can be attached to and detached from the X-ray sensor 3 and can be replaced if it is damaged or when the battery runs out of power. Further, if internal information can no longer be verified owing to damage to a terminal (electrical contact or connector) of the X-ray sensor 3, the internal information can be extracted from the non-volatile storage device 23 and obtained from another device.

Figure 3:
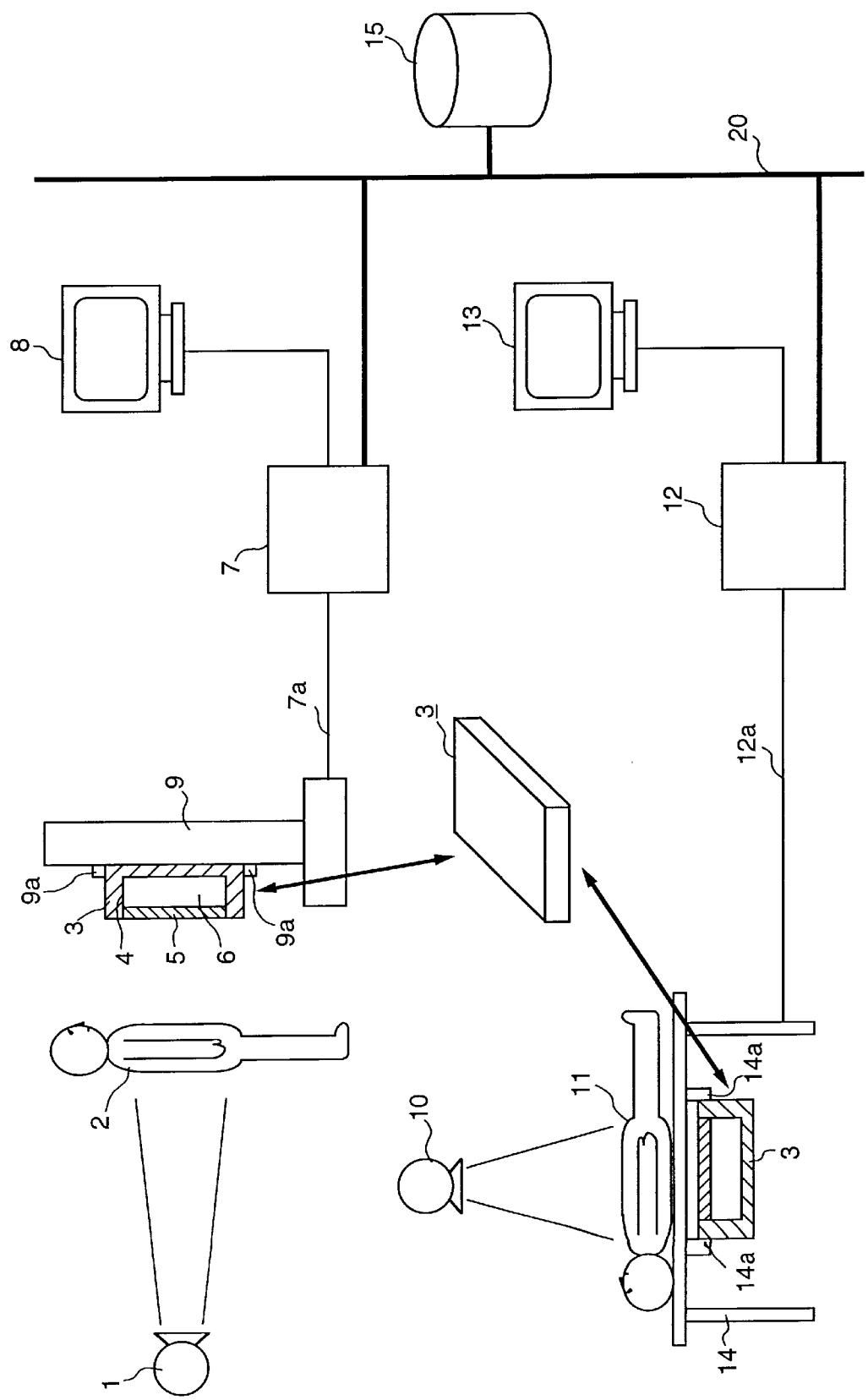
FIG. 3 is a diagram schematically illustrating the overall configuration of an X-ray imaging system according to a second embodiment of the present invention.

FIG. 3 is a diagram schematically illustrating the configuration of an X-ray imaging system according to a second embodiment of the present invention. Components identical with those of the first embodiment will be designated by like reference characters and need not be described again. Primarily a case in which upright X-ray imaging is performed will be described as a typical example.

X-rays output by the X-ray generating device 1 pass through the object 2 and impinge upon the X-ray sensor 3 attached to the stand 9. The X-rays are converted to visible light, which is proportional to the strength of the X-rays, by the phosphor 5 of the solid-state imaging device 4 inside the X-ray sensor 3. The visible light is converted by the photoelectric transducer 6 to an electric charge proportional to the strength of the visible light. This in turn is digitally converted by A/D conversion and then transferred to the controller 7.

In this embodiment, the controller 7 is connected to a database storage device 15 via a network 20 such as the Internet. The database storage device 15 preserves information specific to various X-ray sensors.

The X-ray sensor 3 has the construction shown in FIG. 2. In this embodiment, however, an ID number that has been assigned to the X-ray sensor 3 is stored in the non-volatile storage device 23.

The controller 7 in FIG. 3 goes to the non-volatile storage device 23 to read out the ID number and goes to the database storage device 15 to read out information necessary for imaging, such as defective pixel information and ON time, that is information specific to the X-ray sensor 3 corresponding to the ID. On the basis of the defective pixel information obtained, the controller 7 executes image processing. For example, the controller 7 interpolates information about a defective pixel in the image data by information relating to the surrounding pixels (S102, S103). Since such interpolation processing is well known, it is not described here. In regard to ON time, the lifetime of the solid-state imaging device 4, for example, is influenced greatly by the ON time of the device. Accordingly, information concerning ON time acquired from timekeeping means (not shown) provided in the X-ray sensor 3, for example, is accumulated and stored in the database storage device 15. The ON-time information is obtained and it is determined based upon this information whether it is time to replace the solid-state imaging device 4. If it is determined that replacement time has arrived, processing such as the presentation of a warning display is executed (S102, S103).

If it becomes necessary to alter the information specific to the X-ray sensor 3, as when there is a change in a defective pixel or an increase in ON time in subsequent imaging, the controller 7 rewrites the content of the database storage device 15.

If the X-ray sensor 3 is disconnected from the controller 7 and connected to the other controller 12, the controller 12 reads the ID out of the X-ray sensor 3 and reads the information specific to the X-ray sensor 3 corresponding to the ID number out of the database storage device 15.

Information for specifying conditions of imaging by the solid-state imaging device 4 is stored in the non-volatile storage device 23 according to the first embodiment and in the database storage device 15 according to the second embodiment. However, the converse of this arrangement may be adopted. That is, sensitivity and sharpness or stage information relating to the phosphor in the first embodiment may be mapped to ID numbers and stored in the database storage device 15 of the kind illustrated in the second embodiment and only an ID number may be stored in the non-volatile storage device 23. Alternatively, defective pixel information or ON-time information in the second embodiment may be stored in the non-volatile storage device 23.

Figure 4:
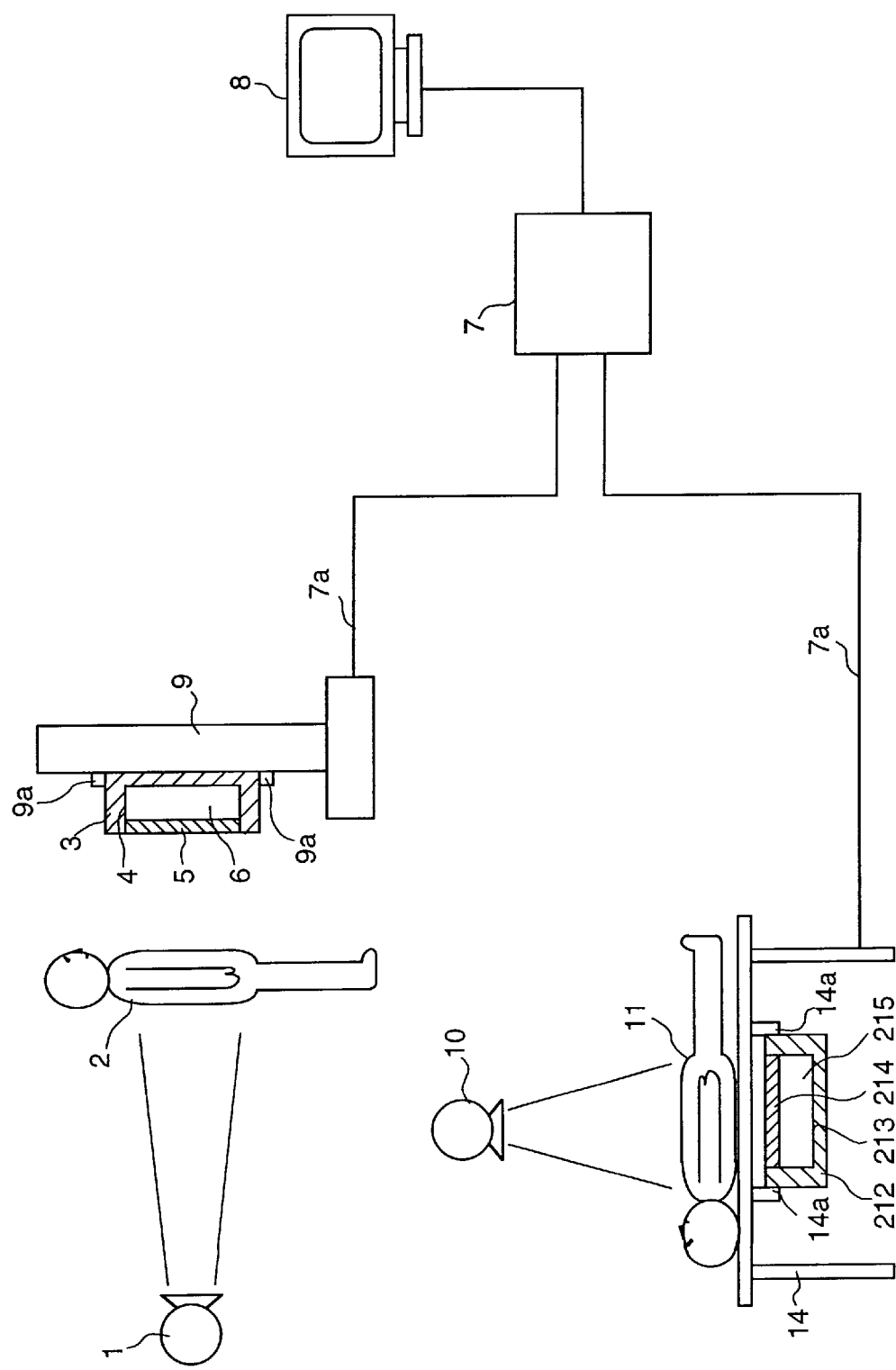
FIG. 4 is a diagram schematically illustrating the overall configuration of an X-ray imaging system according to a third embodiment of the present invention.

FIG. 4 is a diagram schematically illustrating the configuration of an X-ray imaging system according to a third embodiment of the present invention.

This embodiment differs from the earlier embodiments in that an X-ray sensor 212 for the horizontal stand 14 is provided separately of the X-ray sensor 3, and both X-ray sensors are connected to the controller 7 separately via the respective stands. More specifically, according to this embodiment, X-ray sensors are provided separately for upright and prone patients, and the controller 7 and display unit 8 are shared by the X-ray sensors.

X-rays output by the X-ray generating devices 1, 10 pass through the objects 2, 11 and impinge upon the X-ray sensors 3, 212 mounted on the stands 9, 14, respectively.

In a manner similar to that of the X-ray sensor 3, the X-rays are converted to visible light, which is proportional to the strength of the X-rays, by phosphor 214 of a solid-state imaging device 213 inside the X-ray sensor 212. The visible light is converted by a photoelectric transducer 215 to an electric charge proportional to the strength of the visible light. This in turn is digitally converted by A/D conversion and then transferred to the controller 7. In this embodiment, the two X-ray image capture channels can operate one at a time or simultaneously.

At least one of these two X-ray image capture channels has the non-volatile storage device 23 within its X-ray sensor, the non-volatile storage device 23 has information specific to each X-ray sensor in a manner similar to that of the first and second embodiments, and the controller 7 reads out this information as necessary and utilizes the information in a manner similar to that of the first and second embodiments.

FIG. 4 illustrates an example in which the two X-ray image capture channels are connected to the controller 7. However, the number of these channels may be three or more. In addition, an arrangement may be adopted in which each of a plurality of X-ray image capture channels can be attached to and detached from the controller 7.

Figure 5:
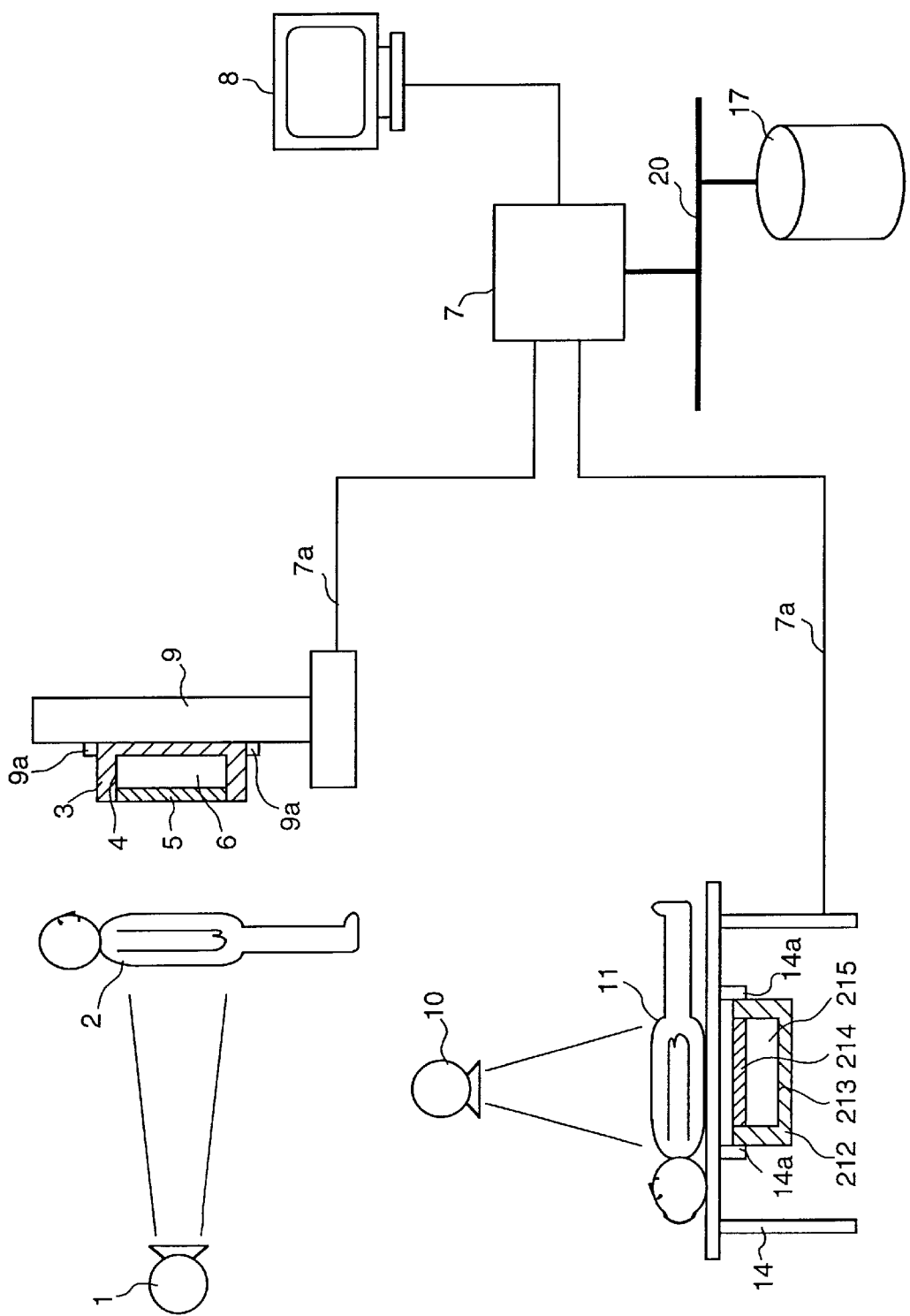
FIG. 5 is a diagram schematically illustrating the overall configuration of an X-ray imaging system according to a fourth embodiment of the present invention.

FIG. 5 is a diagram schematically illustrating the configuration of an X-ray imaging system according to a fourth embodiment of the present invention.

This embodiment differs from the third embodiment in that the controller 7 is connected to database storage device 17 via a network 20 such as the Internet. The database storage device 17 retains information specific to all X-ray sensors. Non-volatile storage devices 23 within the X-ray sensors 3, 212 include ID numbers assigned to the respective X-ray sensors in a manner similar to that of the second embodiment.

In FIG. 5, the controller 7 reads the ID numbers out of the non-volatile storage devices 23, reads information specific to the X-ray sensors 3, 212 corresponding to the ID numbers out of the database storage device 17 and uses this information in a manner similar to that of the first, second and third embodiments.

In this embodiment, the two X-ray image capture channels can operate one at a time or simultaneously. Further, FIG. 5 illustrates an example in which the two X-ray image capture channels are connected to the controller 7. However, the n umber of these channels may be three or more. In addition, an arrangement may be adopted in which each of a plurality of X-ray image capture channels can be attached to and detached from the controller 7.

Described next in some detail will be an example of information for specifying conditions of imaging by the solid-state imaging devices 4, 213 stored in the non-volatile storage device 23 of the foregoing embodiments or in the database storage devices 15, 17. The description that follows deals primarily solely with the first embodiment for the sake of simplicity. However, the description is applicable in similar fashion to the other embodiments as well.

The elements constructing the photoelectric transducer 6 in FIG. 1 have different sensitivities and the amount of electric charge they generate in response to the same amount of light differs. In order to correct for the difference in sensitivity, parallel beams of uniform light are projected upon the photoelectric transducer 6 before the phosphor is affixed thereto, an output value is obtained from each element of the transducer at this time, the output values of all elements are normalized taking the maximum of these values as one, and the normalized values are acquired in the form of a gain table.

The gain table is stored as the above-mentioned information in the non-volatile storage device 23. (In the second and fourth embodiments, gain tables are stored in the database storage devices 15, 17 along with the ID numbers of the corresponding X-ray sensors.) When the X-ray sensor or X-ray image capture channel is connected to the controller 7, the controller 7 reads the gain table out of the non-volatile storage device 23. (In the second and fourth embodiments, the controller 7 reads out an ID number and reads in the gain table that corresponds to this ID number from the database storage device 15 or 17.) As a result, the controller 7 is capable of subjecting the acquired X-ray image to a sensitivity-difference correction using the gain table. More specifically, the difference in sensitivity is corrected by dividing the output of each pixel of the captured image by a value in the corresponding gain table.

The gain table obtained is ascribable solely to the photoelectric transducer 6. The gain table is independent of such imaging conditions as the distance and angle between the X-ray generating device land X-ray sensor 3, the strength of the X-rays, etc., and need not be re-acquired whenever the imaging conditions change. Since a shading correction is not included, the corrected image is equivalent to an X-ray image captured by the conventional film screen system.

Another example of information stored in the non-volatile storage device 23 or in the database storage devices 15, 17 will now be described in detail.

In FIG. 1, imaging through use of X-rays is such that the rate of X-ray absorption differs depending upon the area imaged. This means that X-ray exposure time (X-ray dose) for obtaining an image having the proper density differs for each area.

An example of a method of imaging for solving this problem will now be described. A simple sensor (phototimer) exhibiting sensitivity to X-rays is placed in front or in back of the solid-state imaging device 4, converts captured X-rays to an electrical quantity and integrates the values obtained. If an integrated value exceeds a value that has been set for an imaging area, the phototimer generates an X-ray exposure stop signal and sends this signal to the X-ray generating device 1, in response to which the X-ray generating device 1 stops emitting X-rays. Thus it is possible to render constant the dose of incident X-rays.

One other example of a method of imaging for solving the aforementioned problem involves providing the X-ray generating device 1 with a function for setting exposure time and having the controller 7 acquire the set exposure time from the X-ray generating device 1. In this case a phototimer is not required.

Thus, arrangements in which the X-ray sensor 3 is and is not internally provided with a phototimer are conceivable. In a system in which exposure time cannot be acquired from the X-ray generating device 1, normal imaging cannot be performed in a case where an X-ray sensor not equipped with a phototimer is connected to the system. Accordingly, information indicating whether or not a phototimer has been provided is stored in the non-volatile storage device 23. (In the second and fourth embodiments, the information is stored in the database storage devices 15, 17 along with the ID numbers of the corresponding X-ray sensors.) When the X-ray sensor or X-ray image capture channel is connected to the controller 7, the controller 7 reads the information indicative of absence or presence of the phototimer out of the non-volatile storage device 23. (In the second and fourth embodiments, the controller 7 reads out an ID number and reads in the above-mentioned information that corresponds to this ID number from the database storage device 15 or 17.) When the controller 7 determines based upon this information that the connected X-ray sensor is not applicable to the current system, it is desired in a system in which exposure time, for example, cannot be acquired from the X-ray generating device 1 that a warning indication be presented on the display unit 8 to notify the user when an X-ray sensor devoid of a phototimer has been connected into the system. Furthermore, it is desired that imaging be inhibited in such a case. Conversely, when an X-ray sensor that is equipped with a phototimer is connected into a system that is capable of acquiring exposure time from the X-ray generating device 1, it is possible to carry out control for switching automatically to a mode in which the phototimer is not activated or to a mode in which the X-ray generating device 1 is made to stop generating X-rays on the basis of an integrated value from the phototimer. Accordingly, when the X-ray sensor 3 equipped with a phototimer is connected into a system in which exposure time can be acquired from the X-ray generating device 1, it is possible to adopt a scheme in which a selection screen is displayed on the display unit 8 to allow selection of either a mode in which the X-ray generating device 1 is made to halt the generation of X-rays by utilizing the detection value from the phototimer or a mode in which use is made of exposure time obtained from the X-ray generating device 1, and allowing the operator to make the selection.

A further example of information stored in the non-volatile storage device 23 or database storage devices 15, 17 will now be described in detail.

When X-rays emitted by the X-ray generating device 1 in FIG. 1 pass through the object 2, some of the X-rays are attenuated and advance in the same direction as the incident X-rays, and some of the X-rays are scattered and arrive at the X-ray sensor 3 from different directions. The scattered X-rays impinge upon the solid-state imaging device 4 at positions different from the proper positions of incidence and noise is produced in the image as a result. To prevent this, a grid comprising an array of blades made of a material such as lead that does not transmit X-rays is placed in front of the solid-state imaging device 4 within the X-ray sensor 3, whereby only X-rays that are to properly impinge upon this position are made to impinge upon the solid-state imaging device 4, with the scattered X-rays being shielded from the solid-state imaging device 4.

Since some X-rays that are normally to impinge upon the solid-state imaging device 4 are thus blocked by the grid, grid stripes appear in the captured X-ray image. An example of a method performing X-ray imaging without appearance of grid stripes is to have the controller 7 execute image processing that removes the stripes. For example, with the grid mounted in place, imaging is performed beforehand in the absence of an object, all pixel values are normalized adopting one as the maximum value in the acquired image data, and the normalized values are stored as a table. A density difference between pixels is corrected by dividing each pixel value of the X-ray image by each pixel value in the table. Stripes due to the grid can be eliminated from the X-ray image by such image processing.

Another example of a method of performing X-ray imaging without causing the appearance of grid stripes is to move the grid in a direction orthogonal to the array of grid blades at the time of X-ray exposure and then average the grid shadow. The grid can be moved by a motor operated within the X-ray sensor 3 in sync with X-ray exposure. In this case image processing for removal of grid stripes is unnecessary.

Another example of an imaging method for preventing the occurrence of noise by scattered X-rays involves providing some distance between the object 2 and the X-ray sensor 3 when imaging is carried out. Since scattered X-rays are extremely weak, providing the extra distance causes the scattered X-rays to be attenuated and makes the effects thereof very small. Since the image at such time becomes somewhat larger than actual size, it is required that the controller 7 subject the image data to a size reduction when the image is desired to be displayed in life size. This method makes it possible to dispense with the above-mentioned grid.

Thus, depending upon the method of imaging desired by the user, the X-ray sensor 3 may be equipped with a stationary or movable grid or may not have a grid.

Accordingly, whether or not the X-ray sensor 3 has a grid and, if the sensor does have a grid, the type thereof, is stored in the non-volatile storage device 23 as the above-mentioned information. (In the second and fourth embodiments, the information is stored in the database storage devices 15, 17 along with the ID numbers of the corresponding X-ray sensors.) When the X-ray sensor or X-ray image capture channel is connected to the controller 7, the controller 7 reads the information out of the non-volatile storage device 23. (In the second and fourth embodiments, the controller 7 reads out an ID number and reads in the information that corresponds to this ID number from the database storage device 15 or 17, the information indicating the absence or presence of a grid and the type of grid if the grid is present.)

Thus, the controller 7 is capable of automatically deciding the image processing that is to be applied to the captured X-ray image (S102). For example, if information indicating that the X-ray sensor 3 has been equipped with a stationary grid is obtained, the controller 7 executes the above-described image processing for removing the grid stripes. If information indicating that the X-ray sensor 3 has been equipped with a movable grid or information indicating that the X-ray sensor 3 has not grid is obtained, then the controller 7 does not execute processing for stripe removal.

When an X-ray imaging sensing unit is connected to a processing unit (controller) in accordance with a preferred embodiment of the present invention, the processing unit can acquire information relating to the imaging conditions of the imaging section of the X-ray imaging sensing unit without requiring that the user perform a troublesome information input.

In accordance with a preferred embodiment of the present invention, the processing unit acquires information, which relates to sensitivity or sharpness of an image supplied by the X-ray imaging sensing unit, from the X-ray imaging sensing unit and causes this information to be reflected in image processing.

In accordance with a preferred embodiment of the present invention, the processing unit acquires information, which relates to defective pixels of an image supplied by the X-ray imaging sensing unit, from the X-ray imaging sensing unit and causes this information to be reflected in image processing.

In accordance with a preferred embodiment of the present invention, the processing unit acquires information, which is for compensating for a difference in sensitivity between elements constituting the pixels of the imaging section, from the X-ray imaging sensing unit and causes this information to be reflected in image processing.

In accordance with a preferred embodiment of the present invention, the processing unit acquires information, which indicates whether the X-ray imaging sensing unit is equipped with means for controlling X-ray exposure time, from the X-ray imaging sensing unit and causes this information to be reflected in image processing.

In accordance with a preferred embodiment of the present invention, the processing unit acquires information, which indicates whether the X-ray imaging sensing unit has a grid for preventing X-rays scattered by an object from impinging upon the imaging section, from the X-ray imaging sensing unit and causes this information to be reflected in image processing.

In accordance with a preferred embodiment of the present invention, an ID number is stored in a storage medium of the X-ray imaging sensing unit, whereby the processing unit is capable of acquiring information relating to the imaging conditions of the imaging section of the X-ray imaging sensing unit by referring to a separate storage device based upon the ID number. It is also possible to avoid the need for a large-capacity storage medium in the X-ray imaging sensing unit.

In accordance with a preferred embodiment of the present invention, the X-ray imaging sensing unit is equipped with a storage medium from which information can be read out and to which information can be written by the processing unit, whereby if imaging conditions of the imaging section change with the passage of time, information stored on the storage medium relating to these conditions can be rewritten by the processing unit.

In accordance with a preferred embodiment of the present invention, the X-ray imaging sensing unit can be attached to and detached from the processing unit, thereby making it possible for the X-ray imaging sensing unit to be used by a plurality of processing units.

In accordance with a preferred embodiment of the present invention, an external device issues a warning to the user on the basis of information that has been acquired from the X-ray imaging sensing unit, thereby making it possible to prevent imaging failures before they occur.

The present invention is not limited to the above embodiments and various changes and modifications can be made within the spirit and scope of the present invention. Therefore, to apprise the public of the scope of the present invention, the following claims are made.

What is claimed is:

1. An X-ray image sensing unit having an imaging section for picking up an X-ray image, the X-ray image sensing unit being removably attached to an external processing unit and comprising:
    a transfer device for transferring the image picked up by said imaging section to the processing unit;
    a terminal for connecting or disconnecting said transfer device and the processing unit; and
    a non-volatile storage medium for storing information that specifies data which does not depend on a shading condition, and which is used for correcting a difference in sensitivities of a plurality of pixels of said imaging section.

2. The unit according to claim 1, wherein the information stored on said storage medium further specifies data relating to sharpness of the image picked up by said imaging section.

3. The unit according to claim 1, wherein said imaging section has a phosphor for converting X-rays to visible light and a photoelectric transducer for converting the visible light to electricity, and the information stored on said storage medium further specifies data relating to sensitivity or thickness of the phosphor.

4. The unit according to claim 1, wherein the information stored on said storage medium further specifies data relating to defective pixels of said imaging section.

5. The unit according to claim 1, wherein the information stored on said storage medium further specifies data relating to ON time of said imaging section.

6. The unit according to claim 1, wherein the information stored on said storage medium further specifies data indicating whether or not said X-ray image sensing unit has means for controlling X-ray exposure time.

7. The unit according to claim 1, wherein the information stored on said storage medium further specifies data indicating whether or not said X-ray image sensing unit has a grid for preventing X-rays, which have been scattered by an object, from impinging upon said imaging section.

8. The unit according to claim 1, further comprising a grid for preventing X-rays, which have been scattered by an object, from impinging upon said imaging section, wherein the information stored on said storage medium further specifies data relating to the type of grid.

9. The unit according to claim 1, wherein the information stored on said storage medium includes an ID number of said X-ray image sensing unit.

10. The unit according to claim 1, wherein said storage medium is capable of having information read out and rewritten by said processing unit.

11. An X-ray imaging system comprising:
    an X-ray image sensing unit having an imaging section for picking up an X-ray image, and a processing unit for controlling said X-ray image sensing unit and processing an image supplied by said X-ray image sensing unit;
    said X-ray image sensing unit further having a non-volatile storage medium for storing information that specifies data which does not depend on a shading condition, and which is used for correcting a difference in sensitivities of a plurality of pixels of said imaging section; and
    said processing unit having a decision-making section for reading out the information stored on said storage medium and deciding, on the basis of the information, a method of controlling said X-ray image sensing unit and/or content of processing executed by said processing unit.

12. The system according to claim 11, wherein said X-ray image sensing unit is capable of being attached and detached, and said X-ray image sensing unit and said processing unit each have a terminal for connecting and disconnecting them.

13. The system according to claim 11, wherein said processing unit has a function whereby a storage device on a network is shared by other processing units.

14. The system according to claim 11, wherein an ID number of said X-ray imaging sensing unit is stored on said storage medium, data which does not depend on a shading condition and which is used for correcting a difference in sensitivities of a plurality of pixels of an imaging section of each of a plurality of X-ray image sensing units is stored in a storage device on a network, and said processing unit reads the ID number out of the storage medium and reads data corresponding to this ID number out of said storage device on the network.

15. The system according to claim 14, wherein said imaging section has a phosphor for converting X-rays to visible light and a photoelectric transducer for converting the visible light to electricity, and said storage device further stores data relating to sensitivity or thickness of the phosphor.

16. The system according to claim 14, wherein said storage device further stores data relating to at least one of (1) sharpness of image picked up by said imaging section, (2) defective pixels, (3) ON time of said imaging section, (4) whether or not said X-ray image sensing unit has means for controlling X-ray exposure time or grid for preventing X-rays, which have been scattered by an object, from impinging upon said imaging section, and (5) type of the grid.

17. The system according to claim 11, wherein the processing unit has means for connecting said processing unit to a plurality of X-ray image sensing units.

18. The system according to claim 11, wherein the information stored on said storage medium further specifies data relating to sharpness of the image picked up by said imaging section.

19. The system according to claim 11, wherein said imaging section has a phosphor for converting X-rays to visible light and a photoelectric transducer for converting the visible light to electricity, and the information stored on said storage medium further specifies data relating to sensitivity or thickness of the phosphor.

20. The system according to claim 11, wherein the information stored on said storage medium further specifies data relating to defective pixels of said imaging section.

21. The system according to claim 11, wherein the information stored on said storage medium further specifies data relating to ON time of said imaging section.

22. The system according to claim 11, wherein the information stored on said storage medium further specifies data indicating whether or not said X-ray image sensing unit has means for controlling X-ray exposure time.

23. The system according to claim 11, wherein the information stored on said storage medium further specifies data indicating whether or not said X-ray image sensing unit has a grid for preventing X-rays, which have been scattered by an object, from impinging upon said imaging section.

24. The system according to claim 11, wherein said X-ray image sensing unit has a grid for preventing X-rays, which have been scattered by an object, from impinging upon said imaging section, and the information stored on said storage medium further specifies data relating to the type of grid.

25. The system according to claim 11, wherein said storage medium is capable of having information read out and rewritten by said processing unit.

26. A processing unit, which is connected to one or a plurality of X-ray image sensing units each having an imaging section for picking up an X-ray image, for controlling the X-ray image sensing unit and processing an image supplied by said X-ray image sensing unit, comprising:

a decision-making section for reading out information that specifies data which does not depend on a shading condition, and which is used for correcting a difference in sensitivities of a plurality of pixels of said imaging section, from a non-volatile storage medium possessed by said X-ray image sensing unit, and deciding, on the basis of this information, a method of controlling said X-ray image sensing unit and/or content of processing executed by said processing unit.

27. The processing unit according to claim 26, wherein said imaging section has a phosphor for converting X-rays to visible light and a photoelectric transducer for converting the visible light to electricity, the information stored on said non-volatile storage medium further specifies data relating to sensitivity or thickness of the phosphor, and said decision-making section decides, on the basis of said information, content of sensitivity adjustment processing applied to an image supplied by said X-ray image sensing unit.

28. The processing unit according to claim 26, wherein the information stored on said non-volatile storage medium further specifies data relating to sharpness of the image picked up by said imaging section and said decision-making section decides, on the basis of said information, content of image sharpening processing applied to an image supplied by said X-ray image sensing unit.

29. The processing unit according to claim 26, wherein the information stored on said non-volatile storage medium further specifies data relating to defective pixels of said imaging section and said decision-making section decides, on the basis of said information, content of processing for interpolating defective pixels in an image supplied by said X-ray image sensing unit.

30. The processing unit according to claim 26, wherein the information stored on said non-volatile storage medium further specifies data relating to ON time of said imaging section and said decision-making section decides, on the basis of said information, whether or not to issue a warning to a user.

31. The processing unit according to claim 26, wherein the information stored on said non-volatile storage medium further specifies data relating to whether or not said X-ray image sensing unit has means for controlling X-ray exposure time and said decision-making section decides, on the basis of said information, a method of controlling X-ray exposure time.

32. The processing unit according to claim 26, wherein the information stored on non-volatile storage medium further specifies data relating to whether or not said X-ray image sensing unit has a grid for preventing X-rays, which have been scattered by an object, from impinging upon said imaging section, and said decision-making section decides, based upon said information, whether or not stripe-removal processing is to be applied to an image supplied by said X-ray image sensing unit.

33. The processing unit according to claim 26, wherein said non-volatile storage medium is capable of having information read out and rewritten by said processing unit.

* * * * *

UNITED STATES PATENT AND TRADEMARK OFFICE
CERTIFICATE OF CORRECTION

PATENT NO.   : 6,201,249 B1
DATED        : March 13, 2001
INVENTOR(S)  : Junichi Yamayoshi Page 1 of 1

It is certified that error appears in the above-identified patent and that said Letters Patent is hereby corrected as shown below:

Sheet 6,
Figure 6, "UOPN" should read -- UPON --.

Column 9,
Line 55, "n umber" should read -- number --.

Column 10,
Line 31, "land" should read -- 1 and --.

Column 11,
Line 12, "17.) When" should read -- 17. ¶ When --.

Column 12,
Line 46, "not" should read -- no --.

Signed and Sealed this

Twenty-ninth Day of January, 2002

Attest:

Attesting Officer

JAMES E. ROGAN
Director of the United States Patent and Trademark Office